United States Patent [19]
Burolla

[11] Patent Number: 6,001,230
[45] Date of Patent: Dec. 14, 1999

[54] AUTOMATED CAPILLARY ELECTROPHORESIS APPARATUS

[75] Inventor: Victor Paul Burolla, Livermore, Calif.

[73] Assignee: Beckman Coulter, Inc., Fullerton, Calif.

[21] Appl. No.: 08/055,403

[22] Filed: Apr. 29, 1993

Related U.S. Application Data

[63] Continuation of application No. 07/542,673, Jun. 22, 1990, abandoned, which is a continuation of application No. 07/188,773, Apr. 29, 1988, abandoned.

[51] Int. Cl.$^6$ .......................... G01N 27/26; G01N 27/447
[52] U.S. Cl. .......................... 204/453; 204/451; 204/452; 204/455; 204/601; 204/603; 204/604; 204/605
[58] Field of Search ........................... 204/299 R, 180.1, 204/182.8, 601, 602, 603, 604, 605, 451, 452, 453, 455

[56] References Cited

U.S. PATENT DOCUMENTS

| | | | |
|---|---|---|---|
| 3,238,115 | 3/1966 | Pedersen | 204/300 |
| 3,804,108 | 4/1974 | Ferrari | 137/112 |
| 3,826,621 | 7/1974 | Johnson, Jr. | 23/259 |
| 3,918,913 | 11/1975 | Stevenson et al. | 73/864.24 X |
| 3,932,264 | 1/1976 | Haruki et al. | 204/299 R |
| 3,948,753 | 4/1976 | Arlinger | 204/299 R |
| 3,956,099 | 5/1976 | Israel | 204/299 |
| 4,124,470 | 11/1978 | Dahms | 204/180 |
| 4,294,799 | 10/1981 | Stephens et al. | 422/62 |
| 4,375,401 | 3/1983 | Catsimpoolas | 204/301 |
| 4,455,089 | 6/1984 | Yeung et al. | 356/352 |
| 4,478,095 | 10/1984 | Bradley | 73/864.21 |
| 4,705,616 | 11/1987 | Andresen et al. | 204/299 |
| 4,713,974 | 12/1987 | Stone | 73/864.23 |
| 4,816,123 | 3/1989 | Ogan et al. | 204/183.3 |
| 4,841,151 | 6/1989 | Shope | 250/364 |
| 5,045,172 | 9/1991 | Guzman | 204/299 R |
| 5,085,757 | 2/1992 | Karger et al. | 204/299 R |
| 5,144,139 | 9/1992 | Hillman et al. | 250/341 |

FOREIGN PATENT DOCUMENTS

8605918 U  5/1986  Germany .

OTHER PUBLICATIONS

Honda, S. et al "Evaluation of an Automatic Siphonic Sampler for Capillary Zone Electrophoresis" Journal of Chromatography, vol. 404, No. 2 (Sep. 1987) 313–320.

Rose, Donald Jr. et al "Characterization and Automation of Sample Introduction Methods for Capillary Zone Electrophoresis" Analytical Chemistry (Apr. 1, 1988) 642–648.

Publication by LKB, "Isotachophoresis"; copyrighted 1978.

Frantisek Foret, et al; "On–line Fiber Optic UV Detection Cell and Conductivity Cell for Capillary Zone Electrophoresis"; Electrophoresis (1986) vol. 7, pp. 430–432.

Primary Examiner—Jill Warden
Assistant Examiner—John S. Starsiak, Jr.
Attorney, Agent, or Firm—William H. May; Margaret A. Kivinski

[57] ABSTRACT

An integrated apparatus for capillary electrophoresis which is automated using conveyors which carry vials containing electrolytes and samples, a capillary contained in a modular, portable, and interchangeable cartridge, and actuators for bringing the capillary into flow communication with the fluids in the vials. Electropotential is applied to the ends of the capillary to cause electrophoretic separation. The cartridge may include an opening to allow detection of fluid in the capillary using a detector provided in the apparatus.

28 Claims, 5 Drawing Sheets

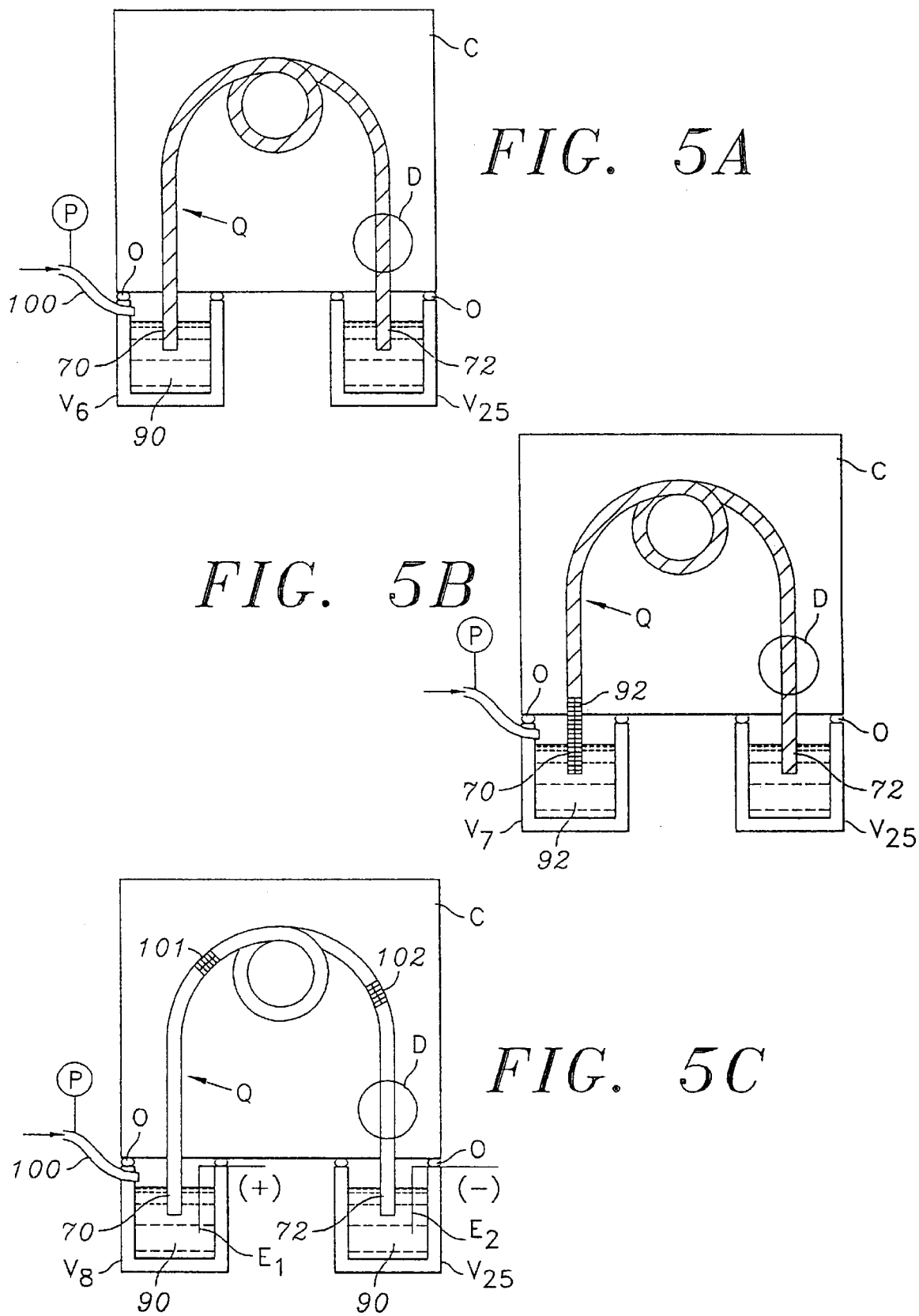

AUTOMATED CAPILLARY ELECTROPHORESIS APPARATUS

This is a continuation of application Ser. No. 07/542,673 filed Jun. 22, 1990, now abandoned, which is a continuation of application Ser. No. 07/188,773, filed Apr. 29, 1998, now abandoned.

This invention relates to capillary electrophoresis. More particularly, an apparatus is disclosed which automates capillary electrophoresis.

BACKGROUND OF THE INVENTION

Capillary electrophoresis is known. An electrolyte filled capillary is injected with sample. The two distal ends of the sample are each emerged in separate electrolyte baths. Each electrolyte bath is communicated with differing electrode potential sufficient for electrophoresis to occur in the capillary.

Electrophoresis is easy to understand. Typically, differing components of a sample subjected to electrophoresis have differing size and differing electric charge. Dependent upon the size of the particles and their charge, a migration of constituents of a sample occurs along the length of a capillary when the capillary is subjected at its distal ends to differing electrical potentials. The discrete particle migration through the capillary is the sum of two effects.

First, and assuming that the capillary is filled with an electrolyte, an overall flow of electrolyte can and does occur due to the difference in electrical potential across the length of the capillary.

Second, and relative to any overall induced flow in the capillary, individual particles of sample will move relative to one another. This movement constitutes the sought after classification due to electrophoresis.

It will be understood that the electrolyte filling in the capillary can be a liquid subject to overall flow or a gel, which is not usually subject to overall flow.

Typically the sample is placed adjacent one end of a capillary. A detector is placed adjacent the opposite end of a capillary. In the migration of the discrete sample constituents relative to the fluid in the capillary, the discrete constituents each form themselves into discrete flowing "bands". These discrete flowing bands are the product of the electrophoresis that are observed to determine both quantity and quality of the sample.

STATEMENT OF THE PROBLEM

There is a need to automate electrophoresis. If the technique can be automated to the point where vials sealed with sample can be automatically subjected to electrophoresis on a basis that is substantially remote, the technique of classification by the electrophoresis can be given an expanded application in analytical techniques.

The reader will understand that insofar as the recognition of the problem constitutes invention, invention is herein claimed.

SUMMARY OF THE INVENTION

The present invention relates to an electrophoresis apparatus which includes a capillary cartridge, containers for samples and electrolyte, and means for applying a potential to effect electrophoresis. The capillary cartridge is positioned with respect to the containers in a manner allowing the ends of the capillary to be in fluid communication with the containers.

An automated apparatus and system for effecting capillary electrophoresis is also disclosed. The system includes two conveyors for conveying septum sealed vials into registry underneath a cartridge containing a capillary for capillary electrophoresis. The capillary is wound in a capillary path in the interior of the cartridge of the cartridge is wound in a serpentine path. The capillary depends at its two distal ends downwardly from the cartridge at two spaced apart exits from the bottom surface of the cartridge, said exits communicated to the distal ends of said path. The vials, each held in a vial holder, are conveyed until one vial on one conveyor underlies one depending distal capillary end and the other vial on the other conveyor underlies the other depending distal capillary end. Once registry of the vials to the distal capillary ends has occurred, the vials are moved upwardly—typically by piston assisted movement of vial holders with respect to the conveyors. Such upward piston assisted movement continues until the vials are pierced at a sealing septum by hypodermics. After piercing of the hypodermics, the piston assisted upward movement continues to thread the hypodermic with either a capillary or an electrode for access to the content to the interior of the vial. The apparatus and process actuates a sequence of vials to produce automated capillary electrophoresis. The sequence includes charging the capillary at a first vial with electrolyte and thereafter injecting from a second and different vial a predetermined amount of sample into the electrolyte filled capillary. After sample injection the sequence includes causing paired third and fourth vials of electrolyte to be communicated to the depending ends of the capillary, communicating electrodes to each of the third and fourth vials to produce the required electric force for capillary electrophoresis and permitting the capillaries to be exposed at its distal ends to the electric forces for a sufficient period of time to cause sample classification due to the electrophoresis. Provision is made in the cartridge immediately adjacent one of the ends thereof for detection of the electrophoretically classified components. The detection schemes including fluorescence, light absorption or reflection, light deflection responsive to electrical changing optical index. Upon completion of the electrophoresis, the capillary is recharged with electrolyte and the process endlessly repeated using differing sequences of vial. The continued electrophoresis either uses the same capillary in the same cartridge or a differing capillary mounted to a different cartridge i.e. an interchangeable, modular and portable cartridge.

OTHER OBJECTS, FEATURES AND ADVANTAGES

An object of this invention is to disclose an apparatus and process for electrophoresis and automated electrophoresis. Accordingly, at least two conveyors are loaded with vials. These vials are preferably septum sealed and registered to a cartridge containing a capillary. One vial on one conveyor is registered underneath a distal end of a capillary depending from a cartridge. The other vial on the other conveyor is registered beneath the opposite distal end of the capillary depending from the cartridge. The vials are thereafter moved vertically to pierce the septum, immerse the capillaries, in the fluid within the vials, and communicate electrodes to the fluid within the vials to effect automated electrophoresis.

A further object of this invention is to automate the injection of electrolyte, and sample to a capillary. According to this aspect, a series of vials are conveyed under one capillary end. A first vial is used to fill the capillary with electrolyte. A second vial is used to inject a small, precisely measured amount of sample. Once these injections have occurred, automated electrophoresis occurs.

An advantage of the disclosed apparatus is that electrophoresis can, for the most part, be automated. By the expedient of placing a series of vials in a conveyor, and appropriately programming the conveyor, e.g. using programmable controller 1 (FIG. 1) sequential analysis of many samples can occur on an automated basis with minimal technician supervision.

A further advantage of the disclosed process is the disposition of a capillary in a cartridge. By the simple expedient of changing the cartridge, the size and length of the capillary can likewise readily be changed i.e. an interchangeable, modular and portable cartridge.

A further object to this invention is to disclose a preferred arrangement of the conveyor. Typically, two concentric and circular conveyors are provided. A first outer circular conveyor having in the order of 24 vials, supplies sequentially electrolyte, for charging the capillary, sample for injecting the capillary and electrolyte for providing electric charge to a depending distal ends of the capillary to cause electrophoresis. A second inner and circular conveyor having in the order of 10 vials supplies electrolyte for the required communication of electric charge for the electrophoresis. As a result, the conveyors, when suitably programmed, can sequentially register vials for a series of electrophoretic classifications, these classifications being essentially remote.

An advantage of this aspect of the invention is that the technician services needed for electrophoresis can be reduced to placing vials in the correct order on a conveyor. The sequential events after placement of the vials on the conveyor are all automated by programmable controller 1.

Yet additional object to this invention is to utilize septum sealed vials for the electrophoresis. According to this aspect, all vials on the conveyors whether including electrolyte or sample are sealed at septums. These septum sealed vials are maneuvered and registered under a cartridge at a distal capillary end and then moved upwardly to effect contact with the capillary. Contact with the capillary is caused by impaling the vial at the septum on hypodermics to penetrate through the septum and form a conduit to the contents of the vials. Once penetration of the septums by the hypodermics has occurred, the hypodermics are threaded with capillaries or electrodes. The threading of the hypodermic with the capillary permits charging of the capillary with electrolyte, the injection of sample and the communication of the end of the capillary to the contents of the vial. The threading of the remaining hypodermic with an electrode permits the communication of electric charge to the contents interior of the vial.

An advantage of this aspect of the invention is that the fluid in the vials are sealed until the moment of their use in the electrophoretic process. Consequently, the process and apparatus here shown is uniquely compatible with laboratory diagnostic routines. Septums sealed samples can await analysis at the disclosed apparatus and be processed at the conveyance of laboratory personnel.

A further object to this invention is to illustrate in combination with the cartridge contained capillary, optical detector apparatus. According to this aspect of the invention, a light source with a conventional condenser light train is focused to a detector path on the analytical apparatus. The disclosed cartridge has two cylindrical protrusions; a first protrusion is for leveling the cartridge, and a second protrusion, placed adjacent the detector aperture in the cartridge, is for registering the detector aperture precisely to the detector light train. By the expedient of providing a filter wheel in the optics, rotating the wheel for the optimum detection, examination of the classified bands in a specimen subject to electrophoretic classification can result.

An important advantage of this aspect of the invention is that most of the detector apparatus is combined to the complex instrumentation exterior of the cartridge. Consequently, the cartridge containing capillary is vastly simplified.

BRIEF DESCRIPTION OF THE DRAWINGS

Other objects, features, and advantages of this invention will become more apparent after referring to the following specification and attached drawings in which:

FIG. 5A–5C are a schematic drawings illustrating in FIG. 5A cartridge contained capillary filled with electrolyte, in FIG. 5B the same cartridge contained capillary charged with sample and in FIG. 5C the capillary undergoing electrophoresis.

Figure 1:
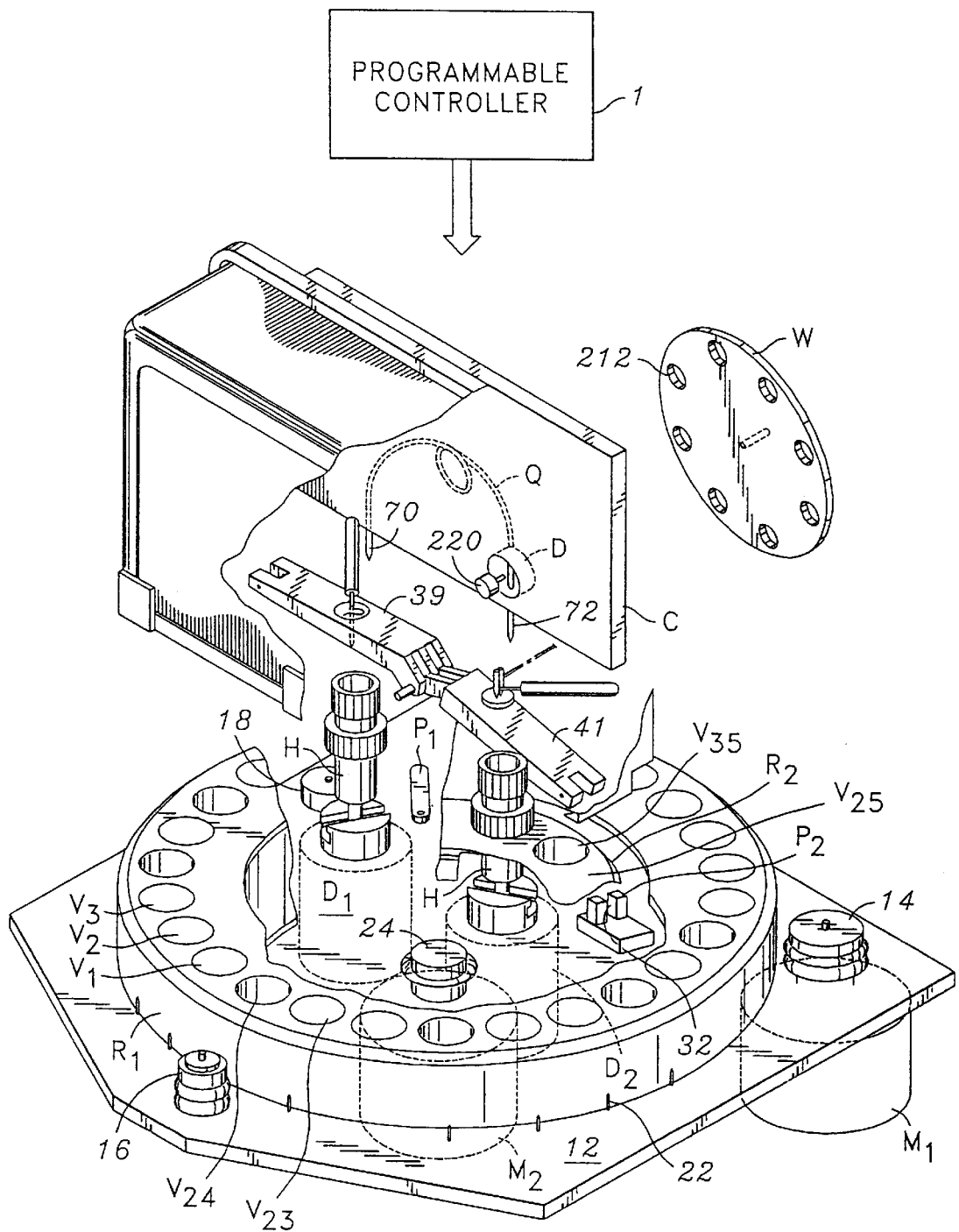
FIG. 1 is a perspective view (partially broken away to show hidden view) illustrating the arrangement of conveyors, actuators, cartridge, piercing mechanism and detector according to one embodiment of the present invention.

Reference to conveyors or autosamplers in a automated capillary electrophoresis instrument may be made to the publication by Rose et al. (Analytical Chemistry, Vol. 60, No. 7, pp. 642–648, Apr. 1, 1988). The present invention is explained herein by reference to the schematically illustrations in the drawings herein.

Referring to FIG. 1 a plate 12 has a first conveyor RI rotatably mounted thereon between wheels 14, 16 and 18. Wheel 14 is rotatable with motor M1 and consequently causes the circular conveyor R1 to rotate as motor M1 turns wheel 14. A detector P1 observes notches 22 configured in conveyor R1. Precise positioning of the conveyor can be made.

Twenty-four vial holders H holding vials V1–V24 are configures in the top of the conveyor R1. As will hereinafter be set forth, these vial holders are selectively registered under a cartridge C (supported by bracket B (FIG. 2) at a depending capillary entrance. By having a plunger D1 cycle the vial holders upwardly and downwardly, sequential filling of the capillary with electrolyte, injection of measured amounts of sample, followed by electrophoresis can sequentially occur.

The operation of inner conveyor R2 is similar. Specifically a motor M2 drives a wheel 24 which along with other idler wheels (obscured from view) cause conveyor R2 to rotate. A position sensor P2 detects the position of the conveyor R2 passing through the groove 32.

Conveyor R2 has vial apertures for receiving vial holders H holding vials V25 through V35 configured in the top thereof. By selectively registering the vials V25 through V35 below the cartridge C at the other distal capillary end, the automated electrophoresis herein can occur. Once registry has occurred, a plunger D2 manipulates the vial upwardly for the automated electrophoresis disclosure set forth herein.

Figure 3:
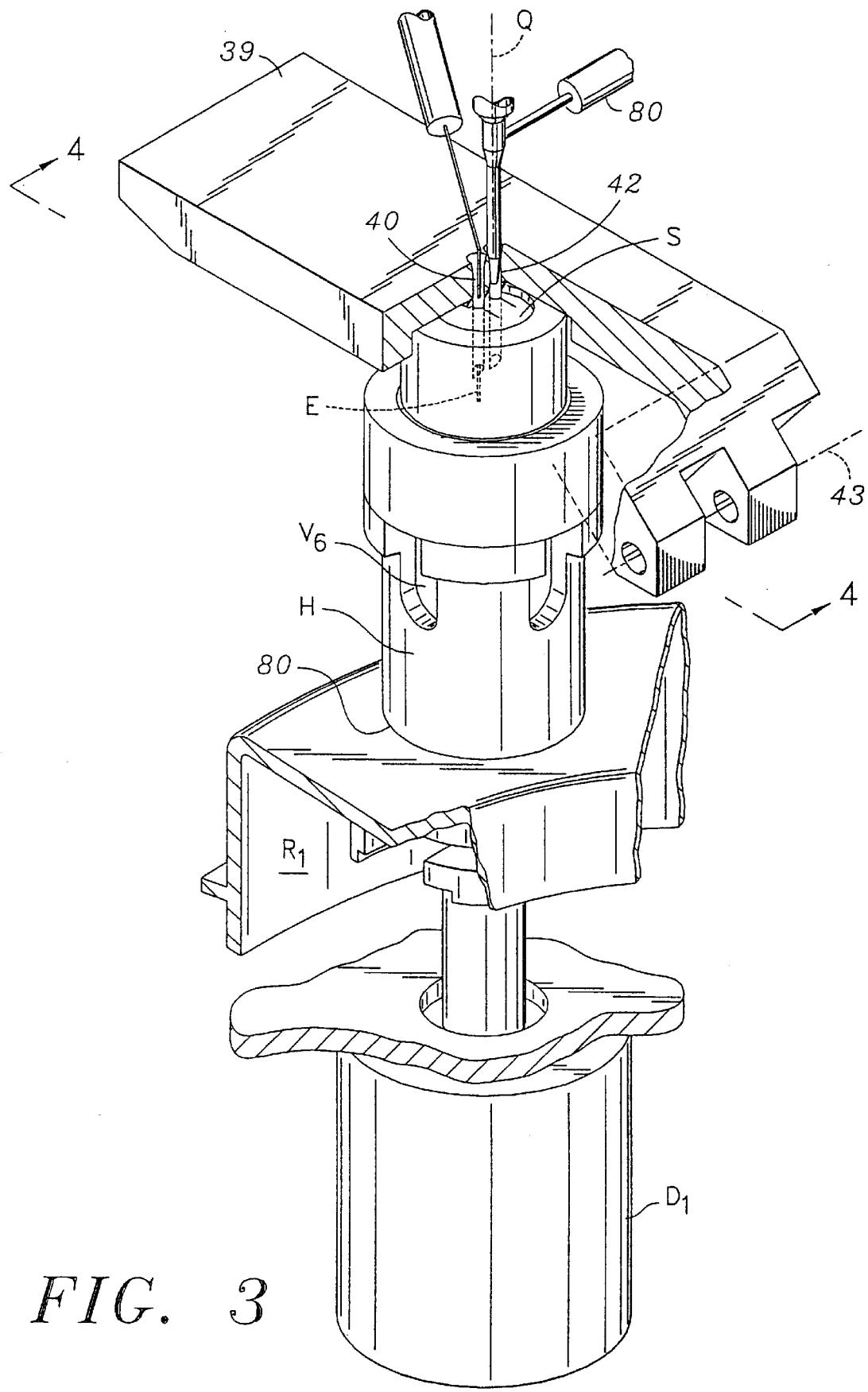
FIG. 3 is a view of the septum piercing hypodermic apparatus, this view being sufficient to understand the mechanics of vial access.

Referring to FIG. 3, it will be understood that conveyor R1 has caused an individual vial, in this case vial V6, to be conveyed in its respective holder H underlying a capillary Q. In this underlying position, plunger D1 pushing the bottom of the holder has moved holder H upwardly. Holder H and the vial V6 contained therein have been impaled upon two hypodermics carried on a pivoted arm 39. These hypodermics are hypodermic 40 containing an electrode E and hypodermic 42 threaded by the capillary Q.

The reader will understand that although not shown in FIG. 3, a similar pivoted arm 41 is present on the other side of the pivot 43 below the other end 72 of the capillary Q, as is apparent in FIG. 3.

Figure 4:
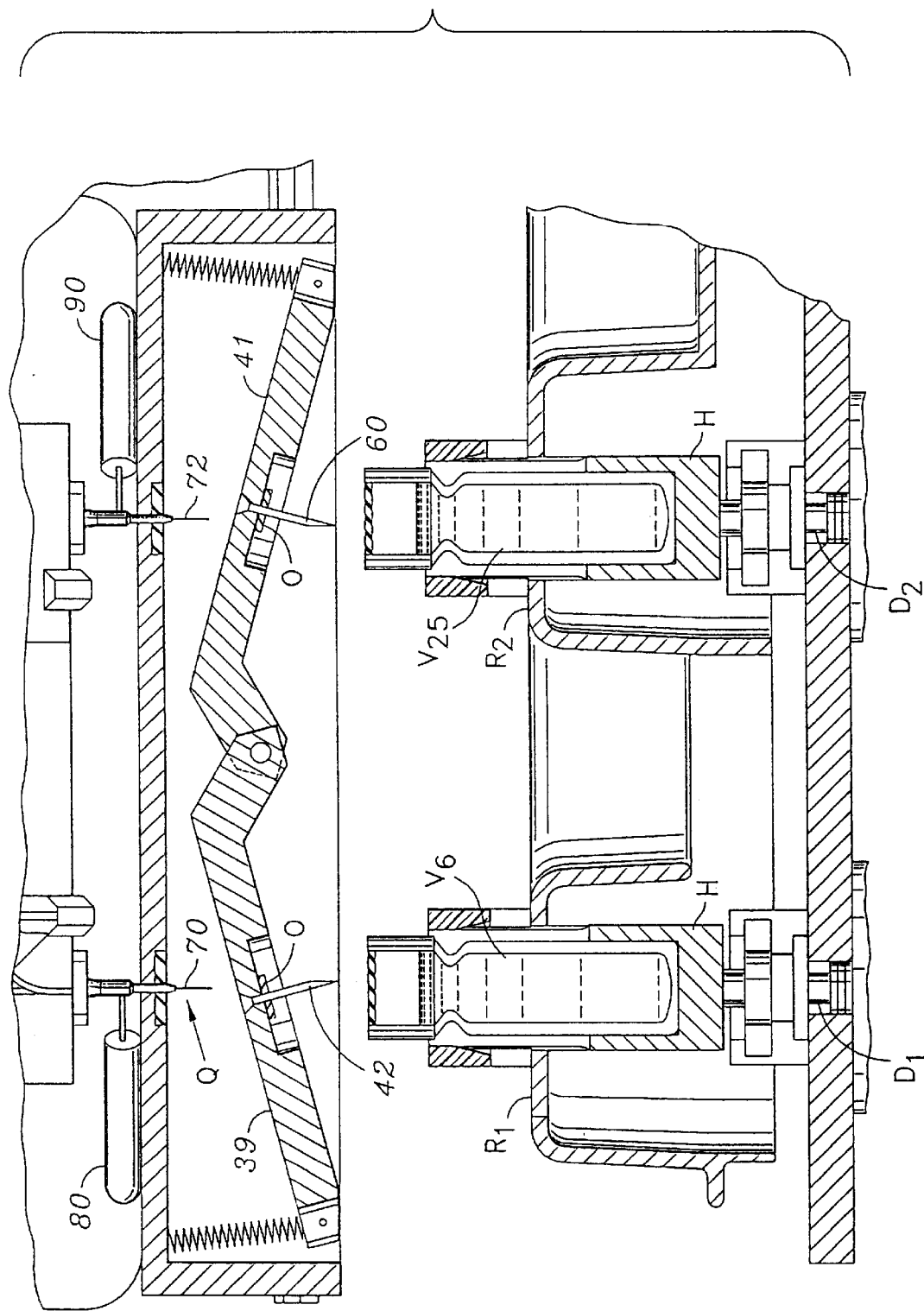
FIG. 4 is a sectional view taken along line 4—4 in FIG. 3 illustrating the bottom of an overlying cartridge with two septum sealed vials each in their own conveyor being registered for access to their sealed contents.

Referring to FIG. 4, the disclosed apparatus can be seen in section. Referring to FIG. 4, two holders H are illustrated with respect to conveyors R1 and R2. Conveyor R1 has caused vial V6 to be positioned underneath hypodermic apparatus (it being noted that the second hypodermic 40 is hidden from view). Similarly, conveyor R2 has positioned vial V25 underlying hypodermic 60, (it being noted that a second electrode is hidden from view).

Referring back to the view of FIG. 1, it can be understood that each vial and hypodermic apparatus underlies an exit of a cartridge. Specifically, two depending capillary ends 70 and 72 depend downwardly.

Referring back to FIG. 3, it can be understood that as the septum S of each vial is pierced, the respective capillaries pierce the septum by threading through the hypodermic. Once piercing of the septum has occurred, the respective hypodermics are threaded. At each vial, threading of one hypodermic occurs with capillary Q. At the other hypodermic, threading with an electrode E occurs.

Referring back to FIG. 4, it will be seen that hypodermic 42 communicates to a source of pressure in conduit 80. Likewise, hypodermic 60 communicates to a source of pressure 90. It will be understood that once registry of the holder H and piercing of the septum by the hypodermics 40, 42 occurs pressure difference in the vials V6 and V25 will cause flow in the capillary Q. For example, if pressure communicated interior of vial V6 is larger than that in V25 (e.g., venting to atmosphere), it will cause flow in the capillary Q from V6 to V25. This flow in the capillary Q will permit charging of capillary Q with electrolyte and thereafter charging of capillary Q with a measured amount of sample.

In order that this may be understood, the schematics of FIGS. 5A, 5B and 5C will now be referred to. It is noted that FIGS. 5A to 5C are schematic representations of an automated electrophoresis apparatus in accordance with the present invention, which also illustrate the generic embodiment of an electrophoresis apparatus of the present invention having the combination of the basic components including a capillary cartridge. Specifically, the generic embodiment of the electrophoresis apparatus of the present invention includes: a capillary cartridge as disclosed herein and in copending applications; containers for samples and electrolyte; and means for applying a potential to effect electrophoresis. The capillary cartridge is positioned with respect to the containers in a manner allowing the ends of the capillary to be in fluid communication with the containers. The conveyors, plungers, etc. and related controls are enhancements to the basic configuration, for implementating an automated electrophoresis apparatus. It is understood that the scope of the present invention covers all electrophoresis apparatus which utilizes a capillary cartridge, irrespective of the specific scheme of automation.

Referring to FIG. 5A, a capillary Q contained in a cartridge C is illustrated. The portable cartridge C includes a body in which is defined a space (e.g. a path for the capillary) in which the capillary Q is supported whereby the ends of the capillary are positioned for fluid communication with the vials V6 and V25. One distal end of capillary Q at 70 is disposed within vial V6. The opposite distal end of the capillary Q is disposed within vial V25. The vials V6 and V25 are sealed against the bottom of the cartridge C by O-ring O.

A conduit 100 supplies pressure to the interior of vial V6. Since capillary end 70 is below the level of electrolyte 90 contained within vial V6, the capillary Q fills with electrolyte. Filling occurs from end 70 to and towards end 72. The general concept of pressure injection of a fluid into a tube has been described in U.S. Pat. No. 3,804,108 to Ferrari and U.S. Pat. No. 3,826,621 to Johnson et al.

Referring to FIG. 5B, vial V6 has been replaced. It has been replaced by the conveyor mechanism with a new vial V7. Vial V7 contains sample.

Again pressure is applied to vial V6. The applied pressure forces the sample 92 into the beginning of the capillary.

Once sufficient sample 92 is injected at end 70 of capillary Q, replacement of the vials again occurs. A vial V8 filled with electrolyte is communicated with end 70 of capillary Q. Likewise, a vial V25 filled with electrolyte is communicated with end 72.

In the schematic of FIG. 5C, electrodes are shown. Specifically, an electrode E1 is shown communicating a positive charge to vial V8 filled with electrolyte 90. Likewise, an electrode E2 is shown communicating electric current to the contents of vial V25 filled with electrolyte 90.

In FIG. 5C, an attempt has been made to show the resultant classification. Specifically, portions of the sample at 101 and 102 have preceded from the original location of the sample adjacent end 70 of capillary Q to that portion of the capillary Q adjacent end 72.

A detector aperture D is shown adjacent end 72 of capillary Q. This detector aperture will here be illustrated as being interrogated by light. The reader will understand that alternate methods of interrogation including the measurement of electrical resistance and the removal of sample for mass spectroscopy may as well be used.

Attention will now be directed to the light train L and its examination of the results of the electrophoresis.

Figure 2:
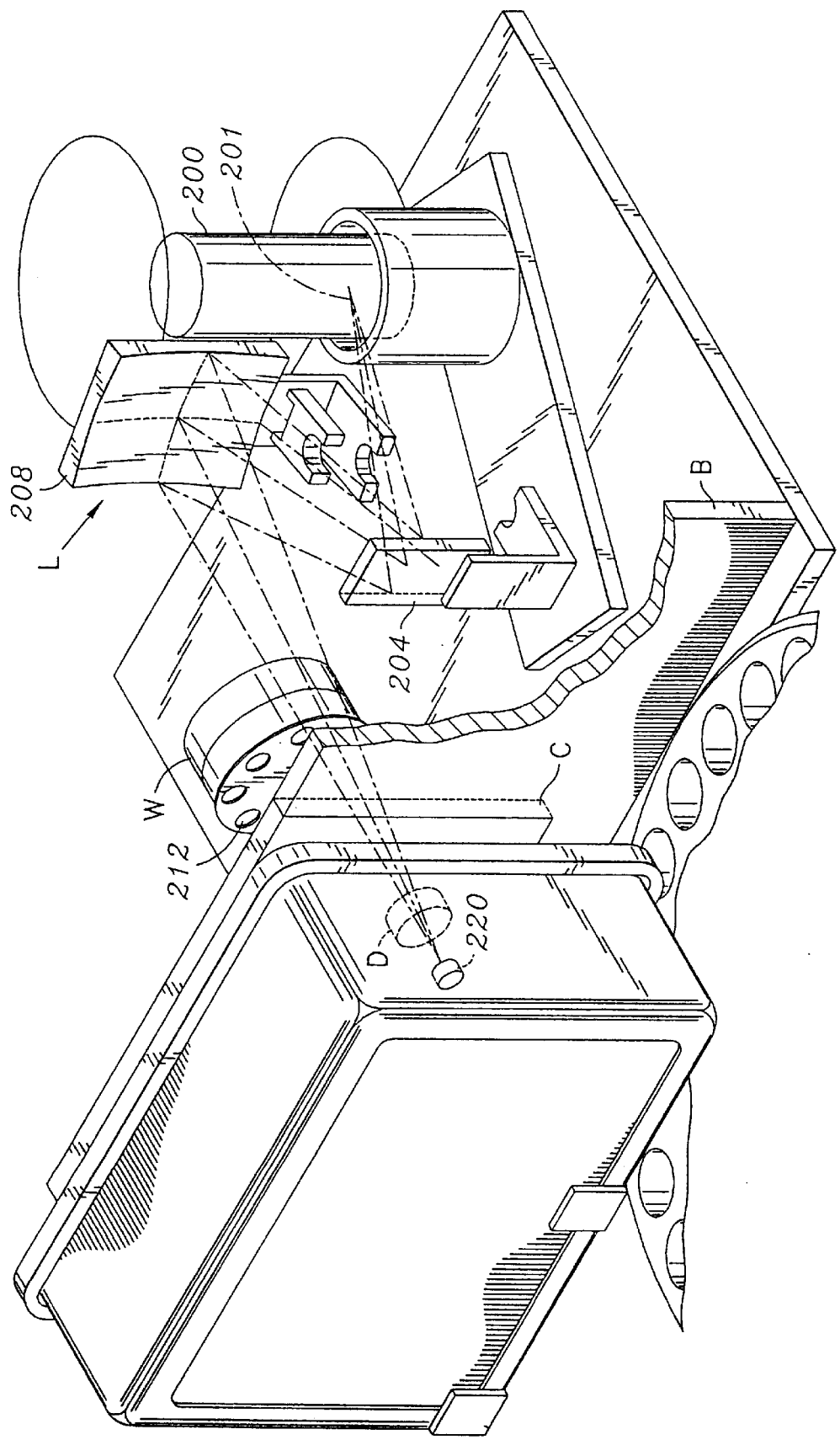
FIG. 2 is a perspective view of the optical detector use in one embodiment of the apparatus of the present invention.

Referring to FIG. 2, light train L can be observed. A light source 200 puts out a point source of light 201. Point source of light is incident upon a plane mirror 204 and a focusing spherical mirror 208. Focusing mirror 208 focuses the light at a wheel W.

Wheel W includes a series of color filters 212. Filter 212 register to the cartridge C. At the detector aperture D light passes through the detector aperture D and onto photosensor 220. It is at the photosensor that recordation of optical measurements can be made.

It will be appreciated that the disclosed instrument additionally includes the possibility of recording resistance as well as other measurements. Such other measurements, such as mass spectroscopy, can be accommodated by running the required electrophoresis in a cartridge C for a given period of time and thereafter removing the cartridge and extracting the concentrated sample bands.

Based on the foregoing description of the cooperative interaction of the capillary cartridge C with various structural elements (e.g. the optical detection apparatus shown in FIG. 2, vial conveyors R1 and R2, ect.) and the fact that the cartridge C can be removed from the apparatus and replaced by another cartridge, one can readily appreciate the modularity, interchangeability and portability attributes of the capillary cartridge.

This application has provided a summary of the combination of components illustrated resulting in the disclosed automated electrophoresis apparatus and process here shown. Separate portions of this apparatus and process have been covered in co-pending patent applications filed of even date herewith which are incorporated by reference. Specifically, continuation Ser. No. 07/614,059, now U.S. Pat. No. 5,198,091 and assigned to the assignee herein completely sets forth possible constructions of the cartridge contained capillary.

Likewise, construction and operation of the vial holder is set forth in co-pending patent application filed of even date herewith. Specifically, a patent application entitled Vial Holder filed Apr. 29, 1988 as Ser. No 07/188,244 (Beckman Instruments Docket No. 8D-555), now U.S. Pat. No. 4,865,090, and assigned to the assignee herein sets forth construction of the vial holder and penetration of the septum of a vial held in the holder by the apparatus disclosed herein.

Finally, the apparatus and process for the injection of sample to a capillary filled with electrolyte is set forth in a co-pending patent application filed of even date herewith. Specifically, a patent application entitled Automated Capillary Injector filed Apr. 29, 1988 as Ser. No. 07/187,760 now abandoned (Beckman Instruments Docket No. 8D-529) and assigned to the assignee herein sets forth a process and apparatus for the precision injection of precise amounts of sample to a capillary filled with electrolyte.

What is claimed is:

1. Apparatus for automated electrophoresis, said apparatus comprising:

a modular, portable and interchangeable cartridge having a bottom;

first and second spaced apart exits through the bottom of said cartridge;

a capillary supported within said cartridge and having its two distal ends depending from the bottom of said cartridge at said spaced apart exits;

first and second vials;

said vials having a body for the containment of electrolyte or sample with an upwardly disposed opening;

means for supporting the cartridge in a manner allowing the distal ends of the capillary to be accessible by the vials and allowing the cartridge to be easily detached for interchanging with another cartridge;

conveyor means for holding and conveying said vials, whereby said first vial may be registered under a depending distal end of said capillary and said second vial can be registered under the other depending distal end of said capillary;

means for positioning said first and second vial for registry under said exits of said cartridge whereby the depending distal ends of said capillary depending from said cartridge may be in communication with the electrolyte or sample in said vial; and means for communicating electropotential to said vials whereby said capillary when filled with electrolyte and sample undergoes electrophoresis between the distal ends of said capillary.

2. The invention of claim 1 and wherein said conveyor means contains a plurality of vials which can be similarly positioned in place of said first vial for registration to said first exit of the cartridge and in place of the said second vial for registration to said second exit of said cartridge.

3. The invention of claim 1 and including detector apparatus registered to said cartridge;

said cartridge including an aperture for observing said capillary;

and means for passing light through said aperture for measurement of electrophoresis classified components within said capillary.

4. A process of electrophoresis comprising the steps of:

providing a capillary having distal ends;

providing a modular, portable and interchangeable cartridge having a bottom;

mounting said capillary to said cartridge so that the distal ends of the capillary protrudes from the bottom of said cartridge at two spaced apart first and second exits;

providing a conveyor for conveying a series of vials containing sample or electrolyte under said first and second exits;

supporting the cartridge in a manner to allow the distal ends of the capillary to be accessible by the vials and to allow the cartridge to be easily detached for interchanging with another cartridge;

registering a vial containing said sample to the end of said capillary at said first exit to immerse said end in sample to inject a quantity of sample to said capillary;

registering vials containing electrolyte to the distal ends of said capillary to immerse the ends of said capillary in electrolyte;

and applying an electropotential across the vials containing electrolyte whereby the sample electrophorese along the length of said capillary.

5. The process of claim 4 further comprising the steps of registering a vial containing electrolyte to one end of the capillary and filling the capillary.

6. The process of claim 4 and wherein said registering step of said vial containing said sample includes pressurizing said vial whereby sample is injected from said vial to the immersed end of said capillary.

7. Apparatus for automated electrophoresis, said apparatus comprising:

a modular, portable and interchangeable cartridge having a bottom, said cartridge defining a path for receiving a capillary;

first and second spaced apart exits through the bottom of said cartridge, said exits communicated to the distal ends of said path;

a capillary supported by said path within said cartridge and having its two distal ends depending from the bottom of said cartridge at said spaced apart exits;

first and second vials for registration to said spaced apart distal ends of said depending capillary at said spaced apart exits;

said vials having a body for the containment of electrolyte or sample with an upwardly disposed opening;

means for supporting the cartridge in a manner allowing the distal ends of the capillary to be accessible by the vials and allowing the cartridge to be easily detached for interchanging with another cartridge;

conveyor means for holding and conveying said vials, whereby said first and second vials can be registered under the depending distal ends of said capillary;

means for moving said first and second vials for registry under said exits of said cartridge whereby the depending distal ends of said capillary depending from said cartridge may be in communication with the sample or electrolyte in said vials; and means for communicating electropotential to said vials whereby said capillary when filled with electrolyte and sample undergoes electrophoresis between the distal ends of said capillary;

said communication means including at least one electrode.

8. The invention of claim 7 and wherein the vials have septum seals, and the invention further comprising means for piercing the septum seals to facilitate penetration of the electrode and the distal ends of said capillary.

9. An automated electrophoresis apparatus comprising:

first and second containers each for holding electrolyte or sample as contents;

a modular, portable and interchangeable cartridge and a capillary supported therein, the capillary having first and second ends and the cartridge having first and second exits through which the ends of the capillary can communicate with the contents in the containers;

positioning means for supporting and positioning the cartridge above the containers in a manner allowing each end of the capillary to be in communication with one of the containers and allowing the cartridge to be easily detached for interchanging with another cartridge; and means for applying electropotential across the length of the capillary.

10. An apparatus as in claim 9 wherein the first and second ends of the capillary extends through the exits, and wherein the positioning means comprises a conveyor which holds and moves the first container along a path below the first cartridge exit.

11. An apparatus as in claim 10 wherein the positioning means further comprises an actuator means for moving said first container toward said first cartridge exit such that the sample or electrolyte in said first container is within reach of the end of the capillary extending through said first exit when said first container is moved to a position below said first exit by the conveyor.

12. An apparatus as in claim 11 wherein the positioning means comprises another conveyor which holds and moves the second container along a path below the second cartridge exit.

13. An apparatus as in claim 12 wherein the positioning means further comprises another actuator means for moving the second container toward said second cartridge exit such that the sample or electrolyte in said second container is within reach of the end of the capillary extending through said second exit when said second container is moved to a position below said second exit by said another conveyor.

14. An apparatus as in claim 9 further comprising a detection means for detecting electrophorectically separated components moving through the capillary.

15. An apparatus as in claim 14 wherein the detection means comprises means for detecting electrophoretically separated components near one of the exits of the cartridge.

16. An apparatus as in claim 14 wherein the cartridge has an aperture exposing a section of the capillary and detection means comprises means for optically detecting electrophorectically separated components moving through the exposed section of capillary.

17. An apparatus as in claim 9 wherein one of the containers has a cover and the positioning means comprises a piercing mechanism disposed between the base of the cartridge and said container for creating an opening in the cover of said container to allow one end of the capillary to enter the container through the opening.

18. An apparatus as in claim 17 wherein the cover of the container is a septum seal.

19. An apparatus as in claim 9 wherein the means for applying electropotential comprises two electrodes each electrically coupled to the contents in the containers at each exit of the cartridge.

20. An apparatus as in claim 19 wherein one of the containers has a cover and the positioning means comprises a piercing mechanism disposed between the base of the cartridge and said container for creating an opening in the cover of said container to allow one of the electrodes to enter the container through the opening.

21. An automated electrophoresis apparatus as in claim 9 wherein the cartridge includes means structured and configured for facilitating cooling of the capillary.

22. An electrophoresis apparatus comprising:

first and second containers for holding sample or electrolyte;

a portable capillary cartridge including a length of capillary having two ends; and a body in which is defined a space in which the capillary is supported whereby the ends of the capillary are positioned for fluid communication with the containers;

the cartridge being supported with respect to the containers in a manner allowing the capillary to be in fluid communication with the contents in the container; and means for applying electropotential to effect electrophoretic separation within the capillary.

23. An electrophoresis apparatus as in claim 22 further comprising detection means for detecting electrophoretically separated components moving through the capillary, wherein the body has a structure which facilitates said detection of electrophoretically separated components.

24. An electrophoresis apparatus as in claim 22 wherein the cartridge includes means structured and configured for facilitating cooling of the capillary.

25. Apparatus for electrophoresis comprising in combination:

a plurality of vials for containing sample or electrolyte;

a portable capillary cartridge;

a capillary supported within said cartridge and having first and second distal ends positioned for fluid communication with said vials;

conveyor means supporting said plurality of vials and bringing respective vials in fluid communication with said first and second distal ends of said capillary;

means for applying an electropotential across said capillary;

a source of radiation;

a detector juxtapositioned with respect to said source to form a detection path therebetween;

a detection passage in said cartridge including at least one aperture defined in said cartridge body adjacent to one of the distal ends of said capillary;

means for registering said capillary to said detection passage to facilitate detection of electrophoretic separation in said capillary from the exterior of said cartridge; and means for alignment of the detection passage in said cartridge body with the detection path between said source and detector.

26. An apparatus as in claim 25 wherein the means for alignment includes support means for supporting said portable capillary cartridge in a given position such that said portable capillary cartridge can be removed and replaced with another cartridge such that the detection passage is precisely positioned with respect to the detection path.

27. The apparatus of claim 25 wherein said cartridge body includes a structure for facilitating circulation of a coolant through said cartridge.

28. The apparatus of claim 27 wherein said coolant is a liquid.

* * * * *